(12) United States Patent
Shen et al.

(10) Patent No.: US 9,555,385 B2
(45) Date of Patent: Jan. 31, 2017

(54) ANIONIC SURFACTANT COMPOSITIONS AND USE THEREOF

(71) Applicant: Dow Global Technologies LLC, Midland, MI (US)

(72) Inventors: Cheng Shen, Shanghai (CN); Jianhai Mu, Shanghai (CN); Xiaohua Wang, Shanghai (CN)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 14/761,661

(22) PCT Filed: Mar. 8, 2013

(86) PCT No.: PCT/CN2013/072360
§ 371 (c)(1),
(2) Date: Jul. 17, 2015

(87) PCT Pub. No.: WO2014/134826
PCT Pub. Date: Sep. 12, 2014

(65) Prior Publication Data
US 2015/0367307 A1   Dec. 24, 2015

(51) Int. Cl.
| | | |
|---|---|---|
| *B01F 17/00* | (2006.01) |
| *C07C 305/10* | (2006.01) |
| *C08F 2/26* | (2006.01) |
| *C07C 309/68* | (2006.01) |
| *C08L 33/02* | (2006.01) |
| *C08L 33/08* | (2006.01) |
| *C11D 1/722* | (2006.01) |
| *C11D 1/83* | (2006.01) |
| *C11D 1/29* | (2006.01) |

(52) U.S. Cl.
CPC ......... *B01F 17/0092* (2013.01); *C07C 305/10* (2013.01); *C07C 309/68* (2013.01); *C08F 2/26* (2013.01); *C08L 33/02* (2013.01); *C08L 33/08* (2013.01); *C11D 1/29* (2013.01); *C11D 1/722* (2013.01); *C11D 1/83* (2013.01); *C11D 1/8305* (2013.01)

(58) Field of Classification Search
CPC ............. C11D 1/722; C11D 1/29; C11D 1/83; C11D 1/8305
See application file for complete search history.

(56) References Cited

U.S. PATENT DOCUMENTS 3,120,505 A * 2/1964 McCubbin .............. C08F 14/06
526/209
3,317,495 A * 5/1967 Jones ...................... C08F 14/06
502/160

(Continued)

FOREIGN PATENT DOCUMENTS

| CN | 1266065 | 9/2000 |
| JP | S5778937 | 5/1982 |

(Continued)

*Primary Examiner* — Michael A Salvitti

(57) ABSTRACT

Provided are surfactant compositions that are useful as alternatives to alkylphenol ethoxylates (APEs) type surfactants in emulsion polymerization. The surfactant compositions comprise: an alkyl alkoxylate sulfate of formula (I): R—O—$(C_3H_6O)_x(C_2H_4O)_y$—$SO_3M$, wherein R, x, y, and M are as defined herein.

7 Claims, 3 Drawing Sheets

(56) References Cited

U.S. PATENT DOCUMENTS

| | | | |
|---|---|---|---|
| 3,565,939 A * | 2/1971 | Beiser | C07C 305/00 510/426 |
| 3,890,239 A * | 6/1975 | Dycus | C09K 8/584 166/270.1 |
| 4,285,356 A * | 8/1981 | Sifferman | F17D 1/17 137/13 |
| 4,293,428 A * | 10/1981 | Gale | C09K 8/584 166/270.1 |
| 4,299,994 A * | 11/1981 | Stahel | C07C 43/10 510/337 |
| 4,395,364 A | 7/1983 | Murata et al. | |
| 4,879,399 A * | 11/1989 | Latella | A61K 8/90 510/127 |
| 6,048,831 A * | 4/2000 | Mori | B01F 17/0028 134/42 |
| 6,147,131 A | 11/2000 | Mork et al. | |
| 6,380,302 B1 * | 4/2002 | Ikenaga | B01F 17/0057 510/495 |
| 6,506,715 B1 | 1/2003 | Schultz et al. | |
| 6,706,931 B2 * | 3/2004 | Edwards | C07C 43/11 568/671 |
| 7,906,474 B2 * | 3/2011 | Varineau | B01F 17/0021 510/360 |
| 9,045,567 B2 * | 6/2015 | Ikenaga | C08F 2/26 |
| 2005/0106118 A1 * | 5/2005 | Sakuma | C11D 1/29 424/70.24 |
| 2006/0148981 A1 * | 7/2006 | Schmidt-Thummes | C08F 212/04 524/745 |
| 2009/0124523 A1 * | 5/2009 | Dol | A61K 8/046 510/119 |
| 2009/0292072 A1 | 11/2009 | Klagge et al. | |
| 2010/0081607 A1 * | 4/2010 | Varineau | C11D 1/722 510/405 |
| 2010/0160206 A1 * | 6/2010 | Chiba | A61K 8/86 510/467 |
| 2010/0305254 A1 * | 12/2010 | Ikenaga | C08F 2/26 524/156 |
| 2011/0098492 A1 * | 4/2011 | Varineau | C11D 1/722 549/554 |
| 2011/0152425 A1 | 6/2011 | Tysak et al. | |
| 2011/0245131 A1 * | 10/2011 | Mu | C11D 1/722 510/351 |
| 2011/0266496 A1 | 11/2011 | Mitsuda et al. | |
| 2012/0115769 A1 * | 5/2012 | Nomura | C11D 1/8305 510/351 |
| 2015/0224462 A1 * | 8/2015 | Shen | C08F 2/26 516/20 |
| 2015/0367307 A1 * | 12/2015 | Shen | C07C 305/10 524/831 |

FOREIGN PATENT DOCUMENTS

| | | |
|---|---|---|
| JP | 1998036885 | 2/1998 |
| JP | 2000345191 | 12/2000 |
| JP | 2006232946 | 9/2006 |
| JP | 2006232947 | 9/2006 |
| JP | 2007077181 | 3/2007 |
| JP | 2010185063 | 3/2009 |
| JP | 2010047655 | 3/2010 |
| WO | 0250006 | 6/2002 |
| WO | 2008118381 | 10/2008 |
| WO | 2011110503 | 9/2011 |

* cited by examiner

ANIONIC SURFACTANT COMPOSITIONS AND USE THEREOF

FIELD

This invention relates to a surfactant composition that is useful as an alternative to alkylphenol ethoxylates (APEs) as an emulsifier for emulsion polymerization. The surfactant composition contains an alkyl alkoxylate sulfate of the chemical structure described below.

BACKGROUND

Surfactants are broadly used as wetting agents in waterborne formulations. For instance, alkylphenol ethoxylates (APEs) are widely recognized as good surfactants in a large variety of applications. APE surfactants, however, suffer from a poor public perception of their environmental compatibility. In addition, they are subject to increasing environmental regulation aimed at reducing their consumption in many applications, including in emulsion polymerization (EP). Therefore, the use of APE type surfactants is declining and suppliers are seeking to provide other surfactants to replace them.

Emulsion polymerization (EP) is a polymerization process in which poorly water soluble monomers are emulsified in water with the aid of emulsifiers and then polymerized with initiators. Surfactants play a key role in emulsion polymerization and in particular, APE based surfactants are generally considered the standard. However, in view of the issues with APE surfactants as discussed above, there is a need for new non-APE materials that exhibit properties suitable for emulsion polymerization. Such properties may include reduced foaming, emulsion formulation stability, and mechanical stability.

The problem addressed by this invention is the provision of new surfactants that are commercially viable alternatives for APE materials in emulsion polymerization.

STATEMENT OF INVENTION

We have now found that surfactant compositions as described herein exhibit a number of useful properties that are comparable to, and in some instances better than, properties observed with APE surfactants. Such properties include, for example, one or more of good surface tension reduction, low and moderate foam with foam collapse, rapid wetting, and formulation stability. Moreover, surfactant compositions of the invention, which are derived from seed oils, are biodegradable. Advantageously, therefore, the surfactant compositions of the invention are viable alternatives to APE surfactants for emulsion polymerization.

In one aspect, there is provided a surfactant composition comprising an alkyl alkoxylate sulfate of formula I:

$$R-O-(C_3H_6O)_x(C_2H_4O)_y-SO_3M \quad (I)$$

wherein x is a real number within a range of from 0.5 to less than 4; y is a real number within a range of from 2 to 15; M is a cation; and R is a mixture of seed-oil based linear alkyl moieties with an alkyl moiety distribution as follows, wherein each wt % is based upon weight of all alkyl moieties present in the distribution and all wt % for each distribution total 100 wt %:

| Carbon Atoms in Alkyl Moiety | Amount |
|---|---|
| $C_6$ | 0 wt %-40 wt % |
| $C_8$ | 20 wt %-40 wt % |
| $C_{10}$ | 20 wt %-45 wt % |
| $C_{12}$ | 10 wt %-45 wt % |
| $C_{14}$ | 0 wt %-40 wt % |
| $C_{16}$-$C_{18}$ | 0 wt %-15 wt % |

In another aspect, there is provided a surfactant composition comprising an alkyl alkoxylate sulfate of formula I, as described above, together with a nonionic alkyl alkoxylate of formula II:

$$R-O(C_3H_6O)_x(C_2H_4O)_y-H \quad (II)$$

wherein x is a real number within a range of from 0.5 to less than 4; y is a real number within a range of from 2 to 15; and R is a mixture of seed-oil based linear alkyl moieties with an alkyl moiety distribution as follows wherein each wt % is based upon weight of all alkyl moieties present in the distribution and all wt % for each distribution total 100 wt %:

| Carbon Atoms in Alkyl Moiety | Amount |
|---|---|
| $C_6$ | 0 wt %-40 wt % |
| $C_8$ | 20 wt %-40 wt % |
| $C_{10}$ | 20 wt %-45 wt % |
| $C_{12}$ | 10 wt %-45 wt % |
| $C_{14}$ | 0 wt %-40 wt % |
| $C_{16}$-$C_{18}$ | 0 wt %-15 wt % |

In a further aspect, there is provided a method of using a surfactant composition as described herein as an emulsifier in an emulsion formulation.

DETAILED DESCRIPTION

Figure 1:
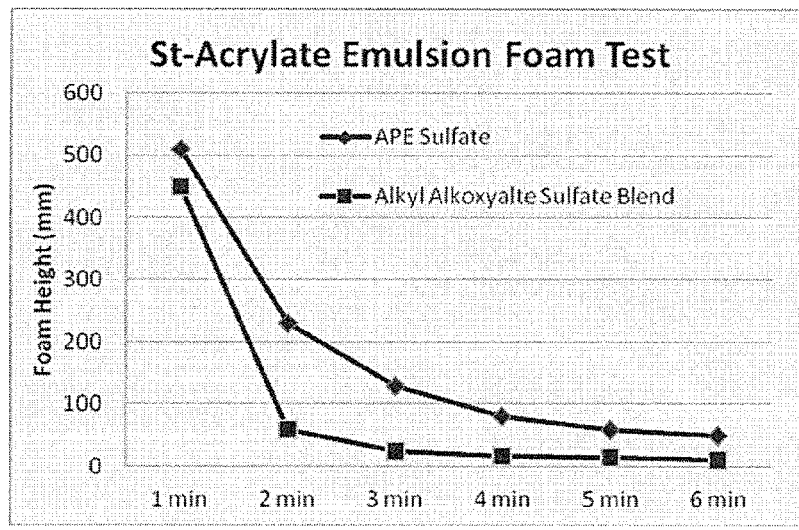
FIG. 1 is plot showing foaming properties for an inventive emulsion according to one embodiment of the invention (example 3-5) and a comparative emulsion (example 3-6).

Unless otherwise indicated, numeric ranges, for instance as in "from 2 to 10," are inclusive of the numbers defining the range (e.g., 2 and 10).

Unless otherwise indicated, ratios, percentages, parts, and the like are by weight.

As noted above, the invention provides a surfactant composition comprising an alkyl alkoxylate sulfate of formula I. The surfactant composition exhibits several useful properties, including one or more of good surface tension reduction, low foam and quick foam collapse, rapid wetting, and calcium ion stability. The advantageous properties render the surfactant composition suitable as an emulsifier for emulsion polymerization.

The alkyl alkoxylate sulfate is of the following formula I:

$$R-O-(C_3H_6O)_x(C_2H_4O)_y-SO_3M \quad (I)$$

In Formula I, each $C_3H_6O$ moiety may also be called a propyleneoxy ($-CH_2-CH(CH_3)-O-$) or PO moiety and each $C_2H_4O$ moiety may also be called a ethyleneoxy or EO moiety. In addition, x is a real number within a range of from 0.5 to 3, y is a real number within a range of from 2 to 15, and M is a cation. Finally, R represents a mixture of seed-oil based linear alkyl moieties with an alkyl moiety distribution in accord with the ranges shown in Table I below.

TABLE 1

Percentages of alkyl moieties

| Alkyl Moiety Carbon Chain Length | Weight Percent |
|---|---|
| $C_6$ | 0-40 |
| $C_8$ | 20-40 |
| $C_{10}$ | 20-45 |
| $C_{12}$ | 10-45 |
| $C_{14}$ | 0-40 |
| $C_{16}$ | 0-15 | wherein each wt % is based upon weight of all alkyl moieties present in the distribution and all wt % for each distribution total 100 wt %.

As shown in Table 1, R can be a mixture of just three alkyl moieties, $C_8$, $C_{10}$ and $C_{12}$. Any one or more of $C_6$, $C_{14}$ and $C_{16}$ alkyl moieties may, but need not be, present in surfactant compositions of the present invention. When present, the amounts of $C_6$, $C_{14}$ and $C_{16}$ alkyl moieties may satisfy any of their respective ranges as shown in Table 1 as long as all weight percentages total 100 wt %.

Formula I above includes variables "x" and "y" that, taken together, establish a degree of alkoxylation in an oligomer distribution. Individually, "x" and "y" represent average degrees of, respectively, propoxylation and ethoxylation. The degree of propoxylation or "x" preferably falls within a range of from 0.5 to less than 4, more preferably within a range of from 0.5 to 3, still more preferably within a range of from 2 to 3, and even more preferably within a range of from 2.5 to 3. In some embodiments, x is 3. The degree of ethoxylation or "y" preferably falls within a range of from 2 to 10, more preferably within a range of from 2 to 8, still more preferably within a range of from 2 to 3, and even more preferably within a range of from 2.5 to 3. In some embodiments, y is 3.

The moiety M in formula I is a cation. Preferably, M is an alkali metal or ammonium, more preferably it is sodium, potassium, or ammonium, and even more preferably M is sodium or ammonium.

A preferred subset of surfactant compositions of the present invention as represented by Formula I include x being within a range of from 2.5 to 3, y is within a range of from 2 to 10 and R has an alkyl moiety distribution as shown in Table 2 below.

TABLE 2

Percentages of alkyl moieties

| Alkyl Moiety Carbon Chain Length | Weight Percent |
|---|---|
| $C_6$ | 0-36 |
| $C_8$ | 22-40 |
| $C_{10}$ | 27-44 |
| $C_{12}$ | 14-35 |
| $C_{14}$ | 5-13 |
| $C_{16}$ | 0-5 |

In other words, the surfactant compositions as shown in Table 2 includes a mixture of at least four alkyl moieties, $C_8$, $C_{10}$, $C_{12}$ and $C_{14}$. Either or both of $C_6$, and $C_{16}$ alkyl moieties may, but need not be, present in surfactant compositions of this preferred subset of the invention. When present, the amounts of $C_6$ and $C_{16}$ alkyl moieties may satisfy any of their respective ranges as shown in Table 1 as long as all weight percentages total 100 wt %.

In some embodiments, in addition to the alkyl alkoxylate sulfate of formula I, the surfactant composition of the invention also comprises a nonionic alkyl alkoxylate of formula II:

$$R\text{—}O\text{—}(C_3H_6O)_x(C_2H_4O)_y\text{—}H \tag{II}$$

In Formula II, x is a real number within a range of from 0.5 to 3, y is a real number within a range of from 2 to 15, and R represents a mixture of seed-oil based linear alkyl moieties with an alkyl moiety distribution in accord with ranges shown in Table 3 below.

TABLE 3

Percentages of alkyl moieties

| Alkyl Moiety Carbon Chain Length | Weight Percent |
|---|---|
| $C_6$ | 0-40 |
| $C_8$ | 20-40 |
| $C_{10}$ | 20-45 |
| $C_{12}$ | 10-45 |
| $C_{14}$ | 0-40 |
| $C_{16}$ | 0-15 | wherein each wt % is based upon weight of all alkyl moieties present in the distribution and all wt % for each distribution total 100 wt %.

As shown in Table 3, R can be a mixture of just three alkyl moieties, $C_8$, $C_{10}$ and $C_{12}$. Any one or more of $C_6$, $C_{14}$ and $C_{16}$ alkyl moieties may, but need not be, present in surfactant compositions of the present invention. When present, the amounts of $C_6$, $C_{14}$ and $C_{16}$ alkyl moieties may satisfy any of their respective ranges as shown in Table 1 as long as all weight percentages total 100 wt %.

In formula II above "x" preferably falls within a range of from 0.5 to less than 4, more preferably within a range of from 0.5 to 3, still more preferably within a range of from 2 to 3, and even more preferably within a range of from 2.5 to 3. In some embodiments, x is 3. In formula 2, "y" preferably falls within a range of from 2 to 10, more preferably within a range of from 2 to 8, still more preferably within a range of from 2 to 3, and even more preferably within a range of from 2.5 to 3. In some embodiments, y is 3.

Preferred nonionic alkyl alkoxylates of formula I include compounds in which x is from 2.5 to 3, y is from 2 to 10 and R has an alkyl moiety distribution as shown in Table 4 below.

TABLE 4

Percentages of alkyl moieties

| Alkyl Moiety Carbon Chain Length | Weight Percent |
|---|---|
| $C_6$ | 0-36 |
| $C_8$ | 22-40 |

TABLE 4-continued

Percentages of alkyl moieties

| Alkyl Moiety Carbon Chain Length | Weight Percent |
|---|---|
| $C_{10}$ | 27-44 |
| $C_{12}$ | 14-35 |
| $C_{14}$ | 5-13 |
| $C_{16}$ | 0-5 |

The surfactant compositions as shown in Table 4 includes a mixture of at least four alkyl moieties, $C_8$, $C_{10}$, $C_{12}$ and $C_{14}$. Either or both of $C_6$, and $C_{16}$ alkyl moieties may, but need not be, present in surfactant compositions of this preferred subset of the invention. When present, the amounts of $C_6$ and $C_{16}$ alkyl moieties may satisfy any of their respective ranges as shown in Table 4 as long as all weight percentages total 100 wt %.

When the nonionic alkyl alkoxylate of formula II is present in the surfactant composition of the invention, the groups R, x, and y in formula I and formula II may be the same or different. In some embodiments, the groups R, x, and y in formula I and formula II are the same.

In some embodiments, the surfactant composition of the invention comprises an alkyl alkoxylate sulfate of formula I and a nonionic alkyl alkoxylate of formula II, wherein the weight ratio of the alkyl alkoxylate sulfate of formula I to the nonionic alkyl alkoxylate of formula II is from 99:1 to 10:90. In some embodiments, the weight ratio is from 95:5 to 50:50, alternatively from 90:10 to 70:30.

In some embodiments, the surfactant composition of the invention further comprises water.

In some embodiments, the surfactant composition of the invention comprises an alkyl alkoxylate sulfate of formula I, a nonionic alkyl alkoxylate of formula II, and water. In some embodiments, the amount of the alkyl alkoxylate sulfate of formula I is from 20 to 75% by weight, preferably from 30 to 60% by weight; the amount of the alkoxylate of formula II is from 0.1 to 30% by weight, preferably from 0.1 to 10% by weight; and the amount of water is from 25 to 75% by weight, preferably from 40 to 70% by weight, based on the total weight of the alkyl alkoxylate sulfate of formula I, the nonionic alkyl alkoxylate of formula II, and the water.

The surfactant composition of the invention may comprise additional additives, such as other surfactants/emulsifiers, and other additives commonly use in emulsion polymerization. In some embodiments, the surfactant composition of the invention further comprises a nonionic surfactant of the formula III: $R^1O-(AO)_z—H$ (III), wherein $R'$ is linear or branched $C_6$-$C_{24}$ alkyl, AO at each occurrence is ethyleneoxy, propyleneoxy, butyleneoxy ($-CH_2-CH(CH_2CH_3)-O-$), or random or block mixtures thereof, and z is from 1 to 50.

The surfactant compositions of the invention exhibit good surface tension reduction, low and moderate foam with foam collapse, rapid wetting, and they provide formulation stability properties, including good $Ca^{2+}$ stability. $Ca^{2+}$ stability may be understood as the tolerance of an emulsion to electrolytes. In downstream application, numerous additives may be mixed with an emulsion, thus, a good $Ca^{2+}$ stability indicates a good formulation stability. As a result of these properties, the surfactant compositions are suitable for use as emulsifiers in emulsion polymerization and indeed may be used as replacements for traditional APE based emulsifiers.

The emulsions in which the surfactant compositions of the invention may be used as emulsifiers are typically aqueous emulsions or dispersions of polymers and/or copolymers which are normally obtainable by emulsion polymerization. There are no particular restrictions as to the nature of the polymers and copolymers in these formulations. Polymers or copolymers based on the following monomer units are preferred: acrylic acid, acrylates, butadiene, methacrylic acid, methacrylates, styrene, and vinyl acetate. Thus for instance in some embodiments an emulsion formulation according to the invention comprises a surfactant composition as described above (including all described embodiments thereof), water, and a monomer.

A person of ordinary skill in the art can readily determine the effective amount of the surfactant composition of the invention that should be used in an emulsion polymerization formulation, via a combination of general knowledge of the applicable field as well as routine experimentation where needed. For instance, in some embodiments, a quantity of from 0.01 to 10 phm (per hundred monomer) by active weight of the surfactant composition, alternatively from 0.1 to 5 phm by active weight of the surfactant composition, or alternatively from 0.2 to 3 phm by active weight of the surfactant composition, based on the total weight of monomers used in the emulsion polymerization, may be suitable.

Alkyl alkoxylates sulfate of formula I may be prepared by the sulfation of nonionic alkyl alkoxylates of formula II. For instance, the Chemithon sulfation process via sulfur trioxide is a sulfation process well known to those skilled in the art. Typically, pre-heated nonionic alkyl alkoxylate (40° C.) may be first contacted with an air-diluted sulfur trioxide in a continuous thin-film reactor, resulting is a quick and exothermic reaction. The crude sulfuric ester acid may be collected at about 55° C. A prompt neutralization by NaOH or $NH_4OH$ to transform sulfuric ester acid to sulfate salt is advantageous to avoid dark color formation and to reduce formation of impurities. Precise control of the molar ratio of $SO_3$ to nonionic alkyl alkoxylate is preferred in order to produce high quality alkyl alkoxylate sulfate.

Nonionic alkyl alkoxylates of formula II as described above may be purchased from commercial vendors or they may be prepared by those skilled in the art using literature techniques (see for instance U.S. Pat. No. 7,906,474, which is incorporated herein by reference). In a typical procedure, the alkoxylate may be prepared in a sequential manner that includes propoxylation (adding PO or propyleneoxy) moieties of an alcohol or mixture of alcohols to form a PO block followed by ethoxylation (adding EO or ethyleneoxy) moieties to form an EO block attached to the PO block, but spaced apart from R which represents alkyl moieties from the alcohol or mixture of alcohols. One may either begin with a mixture of alcohols that provides a distribution of alkyl moieties and then sequentially propoxylate and ethoxylate the mixture or separately propoxylate and ethoxylate select alcohols and then combine such alkoxylates (propoxylated and ethoxylated alcohols) in proportions sufficient to provide a distribution as shown in Table 3 above.

Some embodiments of the invention will now be described in detail in the following Examples.

EXAMPLES

Materials Used in the Examples Include the Following

"Alkyl Alkoxylate Sulfate" means $R-O-(C_3H_6O)_x(C_2H_4O)_y-SO_3M$, where x is 3, y is 3, M is $NH_4$ or Na, and R is derived from a $C_{6-16}$ alcohol blend.

"Nonionic alkyl alkoxylate 1" means R—O—$(C_3H_6O)_x$ $(C_2H_4O)_y$—H, where x is 3, y is 3, and R is derived from a $C_{6-16}$ alcohol blend.

"Nonionic alkyl alkoxylate 2" means $R^2$—O—$(C_3H_6O)_x$ $(C_2H_4)_y$—H, where x is 5.5, y is 9, and $R^2$ is 2-ethyl hexanol (non-inventive material).

"Alkyl Alkoxylate Sulfate Blend" means a blend of the above Alkyl Alkoxylate Sulfate and nonionic alkyl alkoxylate 1.

"APE Sulfate" means nonylphenol-(EO)4 Sulfate (an APE material) available from Rhodia as RHODAPEX® CO-436 (comparative material).

"APE-free sulfate" means a C12-14 alcohol(EO)4 sulfate available from Cognis as DISPONIL® FES-32 (comparative material).

Nonylphenol Ethoxylate: An APE material available from The Dow Chemical Company.

Example 1

Lab-Scale Samples of Alkyl Alkoxylate Sulfate are Prepared Based on Chemithon Sulfation Process

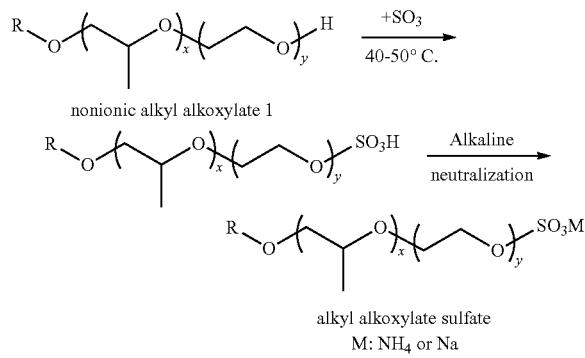

Pre-heated non-ionic alkyl alkoxylate 1 (40° C.) is firstly contacted with an air-diluted liquid sulfur trioxide in a continuous thin-film reactor, which is a quick and exothermic reaction. Molar ratio of $SO_3$ to nonionic surfactant is maintained in the range of 0.85-1.0 by adjustment of nonionic surfactant flow rate in the range of 3-5 kg/h. According to the application needs, we intentionally set this molar ratio range to keep a certain ratio of nonionic surfactants in the final products. Crude sulfuric ester acid (intermediate product) is collected at about 55° C.

A prompt neutralization of crude sulfuric ester acid by NaOH or NH4OH avoids formation of dark color and maintains a good impurity profile. Precise control of the molar ratio of $SO_3$ to non-ionic alkyl alkoxylate 1 produces high quality alkyl alkoxylate sulfate, in particular with reduced formation of 1,4-dioxane.

Formation of the desired Alkyl Alkoxylate Sulfate is confirmed by NMR. The $^{13}C$ NMR spectrum shows the disappearance of —$CH_2OH$ carbon at the chemical shift at δ=61.5 ppm and the presence of —$CH_2OSO_3^-$ carbon at δ=70.0 ppm, which indicates the conversion of nonionic alkyl alkoxylate to alkyl alkoxylate sulfate.

Example 2

Property Testing

Various properties of inventive and comparative compositions are tested. Tests are conducted as follows.

Surface Tension and CMC measurement. Aqueous solution of a surfactant at 4000 ppm is prepared as mother solution and a series of solutions at lower concentrations down to 1 ppm are prepared by diluting the mother solution. The surface tension of each solution is measured following the procedure of GB/T-5549-2010. Surface tension values are plotted against concentration and CMC is determined from the break point of the plot.

Ross-Miles Foam Height test. 300 mL of aqueous solution of surfactant at 0.2% wt. is prepared; then, the measurements are carried out following standard method GB/T-7462-94;

Draves wetting measurement. 1 L of aqueous solution of a surfactant at 0.1% wt. is prepared; cotton cloth is cut at the same size. With reference to standard method GB/T-11983-2008, wetting time to the cotton cloth is recorded in the surfactant solution.

Surfactant $Ca^{2+}$ stability test: measured using standard test GB/T-7381-2010.

Alkaline Resistance test. measured using standard test GB/T-5556-2003;

Viscosity measurement. at room temperature (20° C.), spindle #62 and at 60 rpm; using standard test GB/T-5561-1994.

Testing results are shown in Table 5.

TABLE 5

Surfactant properties of inventive and comparative compositions

| | Inventive example 2-1 Alkyl Alkoxylate Sulfate (component a) | Inventive example 2-2 Alkyl Alkoxylate Sulfate + Nonionic alkyl alkoxylate 1 (component b) (90:10 by wt) | Comparative example 2-3 APE Sulfate (comparative) | Comparative example 2-4 APE-free sulfate (comparative) |
|---|---|---|---|---|
| Active content (wt. %) | 60 | 60 | 58-60 | 30-32 |
| Appearance (20° C.) | clear, pale yellow | clear, pale yellow | clear, pale yellow | clear, pale yellow |
| Surface Tension at CMC (mN/m, 20° C.) | 38 | 33 | 34 | 42 |
| CMC (ppm) | 500 | 125 | 300 | 200 |
| Foam Height (Ross Miles, 0/5 min at 0.2% wt.) | 108/95 | 107/89 | 106/102 | 113/112 |
| Draves wetting (s, 0.1% wt.) | 59.8 +/− 7.8 | 14.7 +/− 0.7 | 5.9 +/− 0.4 | 263.0 +/− 32.9 |
| $Ca^{2+}$ stability ($CaCl_2$, 1% wt.) | 15-20% wt. | 15-20% wt | <2.5% wt. | ≈15% wt. |

TABLE 5-continued

Surfactant properties of inventive and comparative compositions

|  | Inventive example 2-1 Alkyl Alkoxylate Sulfate (component a) | Inventive example 2-2 Alkyl Alkoxylate Sulfate + Nonionic alkyl alkoxylate 1 (component b) (90:10 by wt) | Comparative example 2-3 APE Sulfate (comparative) | Comparative example 2-4 APE-free sulfate (comparative) |
|---|---|---|---|---|
| Anti-alkaline (NaOH, 1% wt.) | 10-15% wt | 10-15% wt | <2.5% wt. | 10-15% wt. |
| Viscosity (cP, at 20° C. & 60 rpm, #62 probe) | 367 | 259 | 120.5 | 63.5 |

As is apparent from Table 5, in comparison with APE sulfate or APE-free sulfate, the inventive compositions showed various useful properties. For instance, the Alkyl Alkoxylate Sulfate of the invention and its blend with nonionic alkyl alkoxylate 1 show comparable properties, including: surface tension at 33 mN/m, is lower than APE sulfate and APE-free sulfate (low surface tension is expected to enhance surfactant wetting ability); CMC is similar as APE-free sulfate, and lower than APE sulfate; foam property improves with regards to both APE-sulfate and APE-free sulfate; wetting property is much better than the APE-free sulfate; and $Ca^{2+}$ stability and alkaline resistance are similar as APE-free sulfate, and superior than APE sulfate.

Example 3

Emulsion Polymerization

Basic Formula of Styrene-Butyl Acrylate Emulsion:
  Monomers include: butyl acrylate, styrene, acrylamide and acrylic acid;
  Initiator is ammonium persulfate;
  Glass transition temperature (Tg): 23° C.;
  Anionic surfactants: 0.51 phm (per hundred monomer); non-ionic surfactants: 0.54 phm.
Basic Formulation of Pure Acrylate Emulsion:
  Monomers include: acrylic acid, butyl acrylate, methacrylic acid;
  Glass transition temperature (Tg): 10° C.;
  Anionic surfactants: 1.0 phm.
Basic Polymerization Procedure of Styrene-Butyl Acrylate Emulsion:
  Pre-emulsify the Alkyl Alkoxylate Sulfate composition with sodium bicarbonate, water and above mentioned monomers. Add the second part of surfactant composition and water into the reactor; start heating to the temperature in the range of 80-90° C.; then, add the first part of ammonium persulfate. Start dropwise addition of pre-emulsion with the second part of ammonium persulfate during 3 h. After addition, keep at the same temperature for 1 h; an emulsion polymerization is performed. After cooling down to room temperature and pH adjustment by aqueous ammonia adjusted to neutral at 40° C., the polymer emulsion is obtained.
Preparation of Other Emulsions:
  For the other emulsions preparation, the procedure described above is followed. Emulsifier composition is changed. See the below Table 6 for the emulsifier details of other emulsions.

TABLE 6

Details of emulsion preparation

| Example | Emulsion type | Surfactant composition | +Non-ionic |
|---|---|---|---|
| Inventive example 3-5 | St-Acrylate | Alkyl Alkoxylate Sulfate Blend (inventive example 2-2) | — |
| Comparative example 3-6 | St-Acrylate | APE-sulfate (comparative example 2-3) | — |
| Inventive example 3-7 | St-Acrylate | Alkyl Alkoxylate Sulfate Blend (inventive example 2-2) | Nonionic alkyl alkoxylate 2 |
| Comparative example 3-8 | St-Acrylate | APE-sulfate (comparative example 2-3) | Nonylphenol Ethoxylate |
| Inventive example 3-9 | Pure-Acrylate | Alkyl Alkoxylate Sulfate Blend (inventive example 2-2) | — |
| Comparative example 3-10 | Pure-Acrylate | APE-free sulfate (comparative example 2-4) | — |

Foaming Property

Low foaming performance is desired in emulsions, which can reduce the use of defoamer in the downstream emulsion applications and also increase the production efficiency. In highly viscous emulsions, low foaming is particularly desired to reduce product defects in both coating and adhesive applications.

Test procedure. The emulsion is diluted to 1% by weight of its solid content. Then, 250 mL of diluted emulsion are poured into a test tube. Air-bubble (air-flow at 1.8 L/s) the aqueous emulsion solution for 1 min; stop air-bubbling and record the foam heights in the next 5 min.—The study is carried out in duplicate, and the results are reproducible at ±5% and the average reported. Comparisons of inventive compositions to commercial APE sulfate and APE-free sulfate are made. Foam test results are shown in FIGS. 1-3.

FIG. 1 compares inventive example 3-5 (see Table 6) and comparative example 3-6. As is apparent, the inventive emulsion exhibited impressive low foam and quick foam collapse relative to the comparative emulsion.

Figure 2:
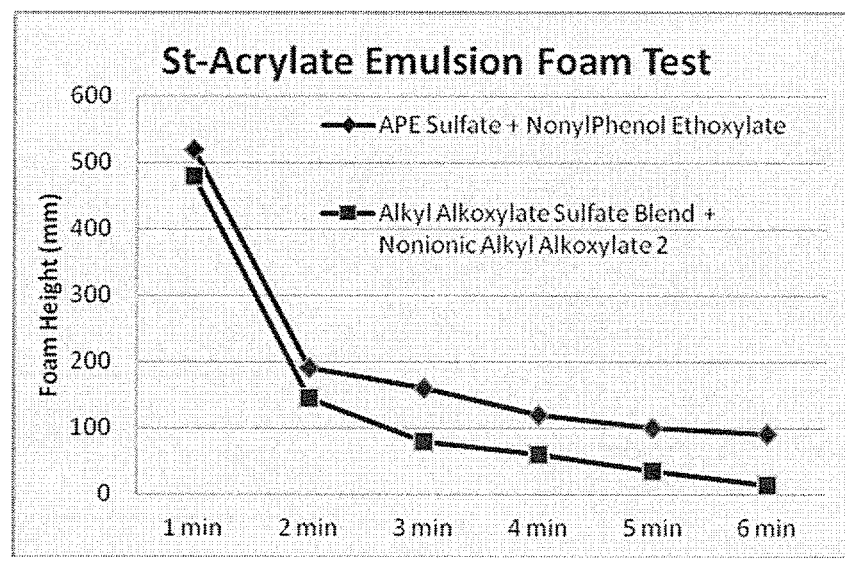
FIG. 2 is plot showing foaming properties for an inventive emulsion according to one embodiment of the invention (example 3-7) and comparative emulsions (example 3-8).

FIG. 2 compares foam properties for inventive example 3-7 versus comparative example 3-8. Again, the inventive emulsion showed better low foam and quicker foam collapse property than the comparative material.

Figure 3:
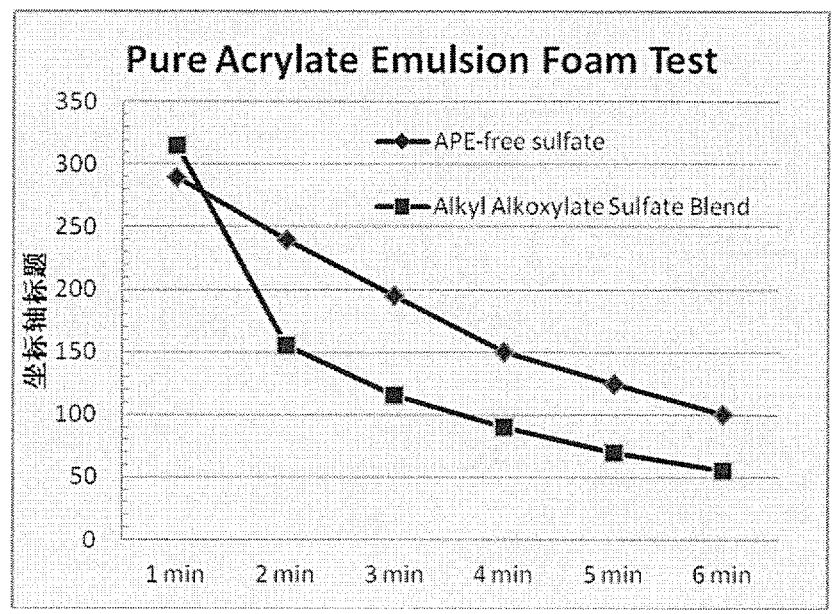
FIG. 3 is plot showing foaming properties for an inventive emulsion according to one embodiment of the invention (example 3-9) and a comparative emulsion (example 3-10).

FIG. 3 compares inventive example 3-9 to comparative example 3-10. The inventive emulsion showed quicker foam collapse than the comparative material.

$Ca^{2+}$ Stability

Test method: Add $CaCl_2$ aqueous solution (concentration at 5 or 10% wt.) into 20 ml of emulsion; store the $CaCl_2$ containing emulsion for 48 h at room temperature; any agglomeration or non-homogeneity present in the emulsion signifies poor $Ca^{2+}$ stability, consequently, failure in the $Ca^{2+}$ stability test. Test results are shown in Table 7.

TABLE 7

Test Results of Ca2+ stability

| | Example | Emulsion type | Surfactant Composition | $Ca^{2+}$ stability |
|---|---|---|---|---|
| Comparison A | Inventive example 3-5 | St-Acrylate | Alkyl Alkoxylate Sulfate Blend (inventive example 2-2) | <10 mL of $CaCl_2$ aq. (10% wt.) |
| | Comparative example 3-6 | St-Acrylate | APE-sulfate (comparative example 2-3) | <4 mL of $CaCl_2$ aq. (5% wt.) |
| Comparison B | Inventive example 3-7 | St-Acrylate | Alkyl Alkoxylate Sulfate Blend (inventive example 2-2) + Nonionic alkyl alkoxylate 2 | >20 mL of $CaCl_2$ aq. (10% wt.) |
| | Comparative example 3-8 | St-Acrylate | APE-sulfate (comparative example 2-3) + NonylPhenol Ethoxylate | <4 mL of $CaCl_2$ aq. (5% wt.) |
| Comparison C | Inventive example 3-9 | Pure-Acrylate | Alkyl Alkoxylate Sulfate Blend (inventive example 2-2) | <10 mL of $CaCl_2$ aq. (10% wt.) |
| | Comparative example 3-10 | Pure-Acrylate | APE-free sulfate (comparative example 2-4) | <10 mL of $CaCl_2$ aq. (5% wt.) |

In Table 7, the comparison A shows that in St-Acrylate emulsion, when no nonionic surfactant is added as emulsifier, the emulsion with Alkyl Alkoxylate Sulfate Blend as emulsifier demonstrates better $Ca^{2+}$ stability than the one with APE sulfate.

The comparison B compares combinations of classic APE sulfate+nonylphenol ethoxylate with Alkyl Alkoxylate Sulfate composition plus alkyl alkoxylate in St-Acrylate emulsion. The emulsion with Alkyl Alkoxylate Sulfate as emulsifier has a better $Ca^{2+}$ stability than the classic APE sulfate and nonylphenol ethoxylate in the surfactant composition. Alkyl Alkoxylate Sulfate Blend offers not only an eco-friendly profile but also better performance on $Ca^{2+}$ stability.

In the comparison C, APE-free Sulfate and Alkyl Alkoxylate Sulfate Blend in Pure-Acrylate emulsion are compared. Again, inventive Alkyl Alkoxylate Sulfate Blend exhibits superior $Ca^{2+}$ stability.

Polymerization Stability

Polymerization stability in emulsion polymerization: collect reaction aggregates by washing, drying at ambient conditions and weigh to determine the amount of aggregates. A percentage by weight of aggregates to the total weight of the monomer indicates the polymerization stability. Small values indicate better polymerization stability.

Particle size and its distribution in polymer emulsion: using Zeta Potential particle analyzer (Malvern Nano ZS), an average particle diameter in the emulsion is measured.

Mechanic stability test: the emulsions (400 g) are rotated for 30 min with 2500 rpm. The generated aggregates are filtered through a 200-mesh filter. The filter residue is rinsed, dried and weighed for comparison. Less aggregate indicates good mechanical stability.

Results. Among those tests, the emulsion with inventive Surfactant Blend achieves similar performance as those with APE or APE-free sulfate emulsifiers.

What is claimed is:
1. A surfactant composition comprising:
an alkyl alkoxylate sulfate of formula I:

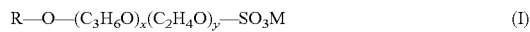

$$R—O—(C_3H_6O)_x(C_2H_4O)_y—SO_3M \quad (I)$$

wherein x is a real number within a range of from 0.5 to less than 4; y is a real number within a range of from 2 to 15; M is a cation; and R is a mixture of seed-oil based linear alkyl moieties with an alkyl moiety distribution as follows wherein each wt % is based upon weight of all alkyl moieties present in the distribution and all wt % for each distribution total 100 wt %:

| Carbon Atoms in Alkyl Moiety | Amount |
|---|---|
| $C_6$ | 0 wt %-40 wt % |
| $C_8$ | 20 wt %-40 wt % |
| $C_{10}$ | 20 wt %-45 wt % |
| $C_{12}$ | 10 wt %-45 wt % |
| $C_{14}$ | 0 wt %-40 wt % |
| $C_{16}$-$C_{18}$ | 0 wt %-15 wt %; | a nonionic alkyl alkoxylate of formula II:

$$R—O—(C_3H_6O)_x(C_2H_4O)_y—H \quad (II)$$

wherein x is a real number within a range of from 0.5 to less than 4; y is a real number within a range of from 2 to 15; and R is a mixture of seed-oil based linear alkyl moieties with an alkyl moiety distribution as follows wherein each wt % is based upon weight of all alkyl moieties present in the distribution and all wt % for each distribution total 100 wt %:

| Carbon Atoms in Alkyl Moiety | Amount |
|---|---|
| $C_6$ | 0 wt %-40 wt % |
| $C_8$ | 20 wt %-40 wt % |
| $C_{10}$ | 20 wt %-45 wt % |
| $C_{12}$ | 10 wt %-45 wt % |
| $C_{14}$ | 0 wt %-40 wt % |
| $C_{16}$-$C_{18}$ | 0 wt %-15 wt %; and | water,
wherein the amount of the alkyl alkoxylate sulfate of formula I is from 20 to 75% by weight, the amount of the nonionic alkyl alkoxylate of formula II is from 0.1 to 30% by weight, and the amount of water is from 25 to 75% by weight based on the total weight of the anionic alkoxylate of formula I, the nonionic alkyl alkoxylate of formula II, and the water.

2. The surfactant composition claim 1 wherein x in formula I and formula II is independently a real number less than or equal to 3.

3. The surfactant composition of claim 1, wherein x in formula I and formula II is independently a real number within a range of from 2-3.

4. The surfactant composition of claim 1, wherein y in formula I and formula II is independently a real number within a range of from 2-10.

5. The surfactant composition of claim 1, wherein x of formula I and formula II is independently from 2.5 to 3 and the alkyl moiety is independently as follows:

| Carbon Atoms in Alkyl Moiety | Amount |
|---|---|
| $C_6$ | 0-36% |
| $C_8$ | 22-40% |
| $C_{10}$ | 27-44% |
| $C_{12}$ | 14-35% |
| $C_{14}$ | 5-13% |
| $C_{16}$-$C_{18}$ | 0-5%. |

6. The surfactant composition of claim 1, further comprising a nonionic surfactant of formula III:

$$R^1\text{—O-(AO)}_z\text{—H} \quad (III)$$

wherein $R^1$ is linear or branched $C_6$-$C_{24}$ alkyl, AO at each occurrence is ethyleneoxy, propyleneoxy, butyleneoxy (—$CH_2$—CH($CH_2CH_3$)—O—), or random or block mixtures thereof, and z is from 1 to 50.

7. A method of emulsion polymerization comprising:
combining an alkyl alkoxylate sulfate surfactant composition, water, and one or more monomers; and
heating the alkyl alkoxylate sulfate surfactant composition, water, and one or more monomers,
wherein the surfactant composition includes:
an alkyl alkoxylate sulfate of formula I:

$$R\text{—O—}(C_3H_6O)_x(C_2H_4O)_y\text{—}SO_3M \quad (I)$$

wherein x is a real number within a range of from 0.5 to less than 4; y is a real number within a range of from 2 to 15; M is a cation; and R is a mixture of seed-oil based linear alkyl moieties with an alkyl moiety distribution as follows wherein each wt % is based upon weight of all alkyl moieties present in the distribution and all wt % for each distribution total 100 wt %:

| Carbon Atoms in Alkyl Moiety | Amount |
|---|---|
| $C_6$ | 0 wt %-40 wt % |
| $C_8$ | 20 wt %-40 wt % |
| $C_{10}$ | 20 wt %-45 wt % |
| $C_{12}$ | 10 wt %-45 wt % |
| $C_{14}$ | 0 wt %-40 wt % |
| $C_{16}$-$C_{18}$ | 0 wt %-15 wt %; and | a nonionic alkyl alkoxylate of formula II:

$$R\text{—O—}(C_3H_6O)_x(C_2H_4O)_y\text{—H} \quad (II)$$

wherein x is a real number within a range of from 0.5 to less than 4; y is a real number within a range of from 2 to 15; and R is a mixture of seed-oil based linear alkyl moieties with an alkyl moiety distribution as follows wherein each wt% is based upon weight of all alkyl moieties present in the distribution and all wt % for each distribution total 100 wt %:

| Carbon Atoms in Alkyl Moiety | Amount |
|---|---|
| $C_6$ | 0 wt %-40 wt % |
| $C_8$ | 20 wt %-40 wt % |
| $C_{10}$ | 20 wt %-45 wt % |
| $C_{12}$ | 10 wt %-45 wt % |
| $C_{14}$ | 0 wt %-40 wt % |
| $C_{16}$-$C_{18}$ | 0 wt %-15 wt %, | wherein the amount of the alkyl alkoxylate sulfate of formula I is from 20 to 75% by weight, the amount of the nonionic alkyl alkoxylate of formula II is from 0.1 to 30% by weight, and the amount of water is from 25 to 75% by weight, based on the total weight of the anionic alkoxylate of formula I, the nonionic alkyl alkoxylate of formula II, and the water.

* * * * *